United States Patent [19]

Postius et al.

[11] Patent Number: 4,656,180
[45] Date of Patent: Apr. 7, 1987

[54] DIAMINE DERIVATIVES AND PHARMACEUTICAL PREPARATIONS CONTAINING THESE COMPOUNDS

[75] Inventors: Stefan Postius, Nürnberg; Rolf Herter, Schwabach; Peter Mörsdorf, Cadolzburg; Helmut Schickaneder, Eckental; Istvan Szelenyi, Schwaig; Kurt H. Ahrens, Nürnberg, all of Fed. Rep. of Germany

[73] Assignee: Ludwig Heumann & Co., GmbH, Fed. Rep. of Germany

[21] Appl. No.: 708,239

[22] Filed: Mar. 5, 1985

[30] Foreign Application Priority Data

Mar. 7, 1984 [DE] Fed. Rep. of Germany ....... 3408327

[51] Int. Cl.$^4$ ..................... A61K 31/34; C07D 401/14
[52] U.S. Cl. .................... 514/316; 546/187;
540/480; 540/481; 546/190; 540/451; 540/596;
546/209; 540/597; 540/598; 546/212; 540/602;
540/603; 546/227; 540/609; 514/183; 544/59;
514/212; 514/222; 544/60; 514/237; 514/255;
544/78; 514/317; 514/326; 544/82; 514/634;
514/649; 544/111; 514/362; 514/365; 544/129;
514/445; 514/438; 544/133; 514/471; 544/146;
544/152; 544/162; 544/165; 544/360; 544/364;
544/367; 544/372; 544/374; 544/398; 544/402;
548/135; 548/161; 548/162; 549/60; 549/65;
549/77; 564/237; 564/306; 564/333

[58] Field of Search ............... 546/187, 190, 209, 212,
546/214, 227; 544/59, 60, 111, 121, 82, 78, 129,
133, 146, 152, 165, 162, 360, 364, 367, 372, 374,
398, 402; 548/161, 162, 135; 549/60, 65, 77;
564/237, 233, 306; 260/239 B; 514/183, 212,
222, 237, 255, 316, 317, 326, 634, 649, 362, 365,
445, 438, 471, 438, 471, 225

[56] References Cited

U.S. PATENT DOCUMENTS 4,062,863 12/1977 Ganellin et al. ..................... 548/342

FOREIGN PATENT DOCUMENTS 3324771 1/1984 Fed. Rep. of Germany ...... 548/135
2098988 12/1982 United Kingdom ................. 546/229

OTHER PUBLICATIONS

Chemical Abstracts, 96:79442; Mar. 8, 1982.
Chemical Abstracts, 96:79443k; Mar. 8, 1982.

Primary Examiner—Robert T. Bond
Attorney, Agent, or Firm—Ostrolenk, Faber, Gerb & Soffen

[57] ABSTRACT

Diamine derivatives corresponding to the general formula I

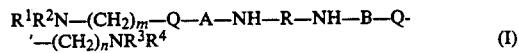

which have a highly selective action on histamine-$H_2$ receptors and are therefore suitable for use as anti-ulcerative agents are described. Processes for the preparation of these compounds and pharmaceutical preparations containing these compounds are also described.

11 Claims, No Drawings

DIAMINE DERIVATIVES AND PHARMACEUTICAL PREPARATIONS CONTAINING THESE COMPOUNDS

DESCRIPTION

This invention relates to new diamine derivatives which have a highly selective action on histamine-$H_2$ receptors, processes for their preparation and pharmaceutical preparations containing these compounds, and the use of these compounds in therapy.

Cimetidine and ranitidine have already been used therapeutically as antiulcerative agents. Both these substances, however, have a relatively short half life and are therefore required to be administered in several daily doses of tablets with dose units of 160 to 300 mg in a therapeutically determined form. There is therefore a need for antiulcerative agents which have a more prolonged action and/or higher activity than cimetidine or ranitidine.

Compounds of this type inhibit gastric secretion stimulated by histamine antagonists due to their specific $H_2$-antagonistic activity [Ash and Schild, "Brit. J. Pharmacol. Chemother. ", 27, 427 (1966) and Black et al, "Nature", 236, 385 (1971)]. The pharmacological activity of these compounds, which is described in more detail below, may be demonstrated on the perfused rat stomach by a modified method according to DE-OS No. 2 734 070 or by determining the $pA_2$-values in vitro on the atrium of the guinea-pig (see Ariens, Molecular Pharmacology, Volume 1, Academic Press, New York, 1964). The $H_2$ antagonistic action can also be demonstrated on waking Heidenhain-Pouch dogs by the method of Black et al, "Nature", 236, 385 (1971) and waking fistulized cats. Such compounds also antagonize the histamine action on the frequency of contraction of the isolated right atrium of the guinea-pig but have no effect on histamine induced contractions of isolated, smooth gastrointestinal muscle when these are produced by $H_2$ antagonists.

Since substances which inhibit histamine-$H_2$ receptors have an inhibitory action both on the basal gastric acid secretion and on the gastric acid secretion induced by gastrine, histamine, metacholine or food, they may be used for the treatment of peptic ulcers caused by excessive gastric acid secretion and the treatment of hyperacidic gastritis.

It is an object of the present invention to provide new inhibitory substances for histamine-$H_2$ receptors with improved and/or more prolonged activity.

The present invention relates to new diamine derivatives as characterised in the claims.

In the general formula I

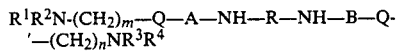

(I)

m and n, independently of one another, have the value 0 or 1. $R^1$, $R^2$, $R^3$ and $R^4$ represent, independently of one another, hydrogen, $C_{1-10}$-alkyl, in particular $C_{1-3}$-alkyl such as methyl or ethyl, $C_{5-6}$-cycloalkyl, i.e. cyclopentyl or cyclohexyl, amino, lower alkylamino, in particular propyl, ethyl or methylamino, or di-lower alkylamino, in particular dipropyl, diethyl or dimethyl alkylamino. $R^1$ and $R^2$ and/or $R^3$ and $R^4$ may represent, together with the nitrogen atom at which they are attached, a 5- to 8-membered alicyclic heterocyclic ring which may be substituted or unsubstituted. Preferred examples of such rings are the pyrrolidine, methylpyrrolidine, morpholine, thiomorpholine, piperidine, methylpiperidine, N-methylpiperazine, homopiperidine, heptamethyleneimino and octamethyleneimino ring. The pyrrolidine and piperidine ring are preferred. Regardless of the value of m and n, $R^3$ and $R^4$ may together form the group $(NH_2)_2C=$. When m has the value 0, $R^1$ and $R^2$ may together form the group $(NH_2)_2C=$.

In the general formula I, Q and Q', which may be identical or different, denote a furan, thiophene, thiazole or benzene ring, the benzene ring being preferred. The benzene ring is preferably inserted in the remainder of the molecule in the 1,3- or 1,4-position. The furan ring is preferably inserted in the remainder of the molecule in the 2,5-position. The thiophene ring is preferably inserted in the remainder of the molecule in the 2,4- or 2,5-position. The thiazole ring is preferably inserted in the remainder of the molecule in the 2,4-position. A and B represent, independently of one another, the group $O-(CH_2)_q$, $O-CH_2-CHOH-CH_2$ or $CH_2-X-CH_2-Y-(CH_2)_p$, preferably the group $O-CH_2-CHOH-CH_2$. In the first mentioned group, q has the value 2,3 or 4, preferably 2 or 3. In the last mentioned group, X represents a sulphur or oxygen atom or the group CHOH, preferably an oxygen atom. The value of p is 1 or 2 and Y represents a single bond or the group CHOH. R represents the ring system corresponding to the formula

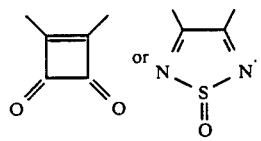

In a preferred group of compounds, Q in the general formula I represents a benzene ring which is inserted in the remainder of the molecule by linkage in the 1- and 3-position or the 1- and 4-position, preferably in the 1- and 3-position. In that case, m and n each have the value 1. $R^1$ and $R^3$, which in this case are identical, preferably represent a hydrogen atom or a linear $C_{1-10}$-alkyl, in particular a $C_{1-3}$-alkyl group, such as, for example, methyl, ethyl, propyl or isopropyl. $R^2$ and $R^4$, which are in this case identical, represent $C_{5-6}$-cycloalkyl such as cyclopentyl or cyclohexyl, preferably cyclohexyl. When $R^1$ and $R^3$ represent linear $C_{1-10}$-alkyl, in particular $C_{1-3}$-alkyl, such as, for example, methyl, ethyl or propyl, then $R^2$ and $R^4$ preferably also represent linear $C_{1-10}$-alkyl, in particular $C_{1-3}$-alkyl as defined above.

Another preferred group of compounds according to the invention is characterised in that $R^1$ and $R^2$ and/or $R^3$ and $R^4$ represent, together with the nitrogen atom to which they are attached, a substituted or unsubstituted 5- to 8-membered alicyclic heterocyclic ring such as, for example, a pyrrolidine, methylpyrrolidine, morpholine, thiomorpholine, piperidine, methylpiperidine, N-methylpiperazine, homopiperidine, heptamethyleneimino or octamethyleneimino ring, in particular a pyrrolidine ring or piperidine ring. In that case, A in the general formula I represents a group $O—(CH_2)_2$, $O—CH_2—CHOH—CH_2$, $CH_2—O—CH_2—CHOH—CH_2$, $CH_2—CHOH—CH_2$ or $CH_2—CHOH—CH_2CH_2$, R represents the ring system corresponding to the formula

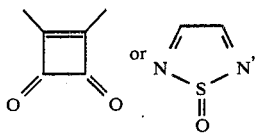

B represents a group as described for A, while Q and Q' represent a benzene ring inserted in the 1,3-position.

Particularly preferred are compounds in which m and n both have the value 1, both $R^1$ and $R^2$ and the attached nitrogen atom and $R^3$ and $R^4$ together with the attached nitrogen atom represent in each case a pyrrolidine or piperidine ring, Q and Q' represent each a benzene ring inserted in the remainder of the molecule by bonds in the 1- and 3-position, A represents the group $O—(CH_2)_3$ or A and B both represent the group $O—(CH_2)—CHOH—CH_2$ or A represents the group $O—(CH_2)_3$ and B represents the group $O—CH_2—CHOH—CH_2$ while R represents one of the ring systems indicated above.

In another particularly preferred group of compounds of the type described above, A represents the group $O—(CH_2)_q$, $O—CH_2—CHOH—CH_2$, $CH_2—O—CH_2—CHOH—CH_2$, $CH_2—CHOH—CH_2$ or $CH_2—CHOH—CH_2CH_2$, and R represents one of the ring systems mentioned above while B represents the group $CH_2—X—CH_2—Y—(CH_2)_p$, where X represents a sulphur atom or the group CHOH. Y is in this case a single bond or the group CHOH; p has the value 1 or 2, and Q' represents a furan ring inserted in the remainder of the molecule in the 2,5-position or a thiophene ring inserted in the remainder of the molecule in the 2,5- or 2,4-position.

Compounds in which m and n each have the value 1, $R^1$ and $R^2$ together with the nitrogen atom attached thereto represent a pyrrolidine or piperidine ring and $R^3$ and $R^4$ together with the nitrogen atom attached thereto represent a piperidine ring or they represent each a methyl group, are particularly preferred. In these particularly preferred compounds, Q represents a benzene ring which has been inserted in the remainder of the molecule by bonds in the 1- and 3-position while A represents the group $O—(CH_2)_3$ or $O—CH_2—CHOH—CH_2$. B in this case represents the group $CH_2—S—CH_2CH_2$ and Q' represents a furan ring inserted in the remainder of the molecule in the 2,5-position of a thiophene ring inserted in the remainder of the molecule in the 2,5- or 2,4-position. R represents one of the ring systems mentioned above.

Another very particularly preferred group of compounds according to the invention is characterised in that Q and Q' in the general formula I represent each a furan ring inserted in the 2,5-position or a thiophene ring inserted in the remainder of the molecule in the 2,5- or 2,4-position. In that case, both m and n have the value 1, $R^1$, $R^2$, $R^3$ and $R^4$ conform to the definitions given above, A preferably represents the group $CH_2—S—CH_2CH_2$ or $CH_2—S—CH_2—CHOH—CH_2$, and R represents one of the ring systems indicated above.

One group of compounds which should be particularly considered is characterised in that m and n both have the value 1, $R^1$, $R^2$, $R^3$ and $R^4$ represent, independently of one another, a methyl or ethyl group, Q and Q' represent, independently of one another, a furan ring inserted in the remainder of the molecule in the 2,5-position or a thiophene ring inserted in the 2,5- or 2,4-position, A and B, which are in this case identical, represent each the group $CH_2—S—CH_2CH_2$, and R represents one of the ring systems mentioned above.

Compound in which Q in the general formula I represents a benzene ring inserted in the remainder of the molecule in the 1,3-position and Q' represents a thiazole ring inserted in the 2,4-position are very particularly preferred. In that case, m has the value 1 and n the value 0 while $R^1$ and $R^2$ represents, independently of one another, a pyrrolidine ring or piperidine ring, $R^3$ and $R^4$ together represent the group $(NH_2)_2C=$, and A, B and R have the meanings indicated above.

The following compounds are particularly preferred: 1-N-[3-(3-piperidylmethyl)-phenoxy-2-hydroxy-propyl]-2-N'-[3-(3-piperidylmethyl)-phenoxy-propyl]-diaminocyclobutene-3,4-dione; 1,2-bis-N,N'-[3-(3-piperidylmethyl)-phenoxy-2-hydroxypropyl]-diaminocyclobutene-3,4-dione and 3,4-bis-[2-hydroxy-3-[3-(1-piperidylmethyl)-phenoxy]-propyl]-amino-1,2,5-thiadiazole-1-oxide.

The compounds according to the invention may be prepared by a process which is characterised in that for the preparation of symmetric compounds, a derivative corresponding to the general formula II

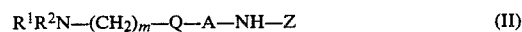

which may be prepared in known manner in situ and in which $R^1$, $R^2$, m, Q and A have the meaning indicated in claim 1 and Z represents a ring system corresponding to the formula

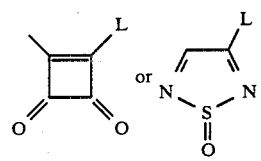

wherein L represents a methoxy, ethoxy or butoxy group as exit group, is reacted with preferably equimolar quantities of an amine corresponding to the general formula III

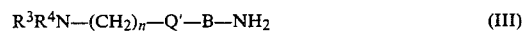

wherein $R^3$, $R^4$, n, Q' and B have the meanings defined above, in an alcoholic solvent such as methanol, ethanol, isopropanol or butanol, preferably ethanol, and the compound obtained is optionally converted into a physiologically acceptable salt thereof.

The reaction is normally carried out at a temperature from room temperature to the boiling point of the solvent used. Working up and isolating the end product are also carried out by the usual methods, for example, by crystallisation, etc.

For the preparation of asymmetric compounds, a derivative corresponding to the general formula II as described above may be reacted with an amine corresponding to the general formula III in which $R^3$, $R^4$, n, Q' and B do not have the same meaning as $R^1$, $R^2$, m, Q and A, to form the corresponding compound according to the invention.

The invention also covers the stereochemically isomeric compounds of formula I in the form of physiologically acceptable hydrates and salts thereof with inorganic and organic acids. These salts may be formed, for example, with mineral acids such as hydrochloric, hydrobromic or hydriodic acid, phosphoric acid, metaphosphoric acid, nitric acid or sulphuric acid, or with organic acids such as formic acid, acetic acid, propionic acid, phenylacetic acid, tartaric acid, citric acid, fumaric acid, methanesulphonic acid etc.

The compounds according to the invention may be made up into any desired formulations for administration. The invention therefore also covers pharmaceutical preparations containing at least one compound according to the invention for use in human or veterinary medicine. Such medicaments may be prepared by the conventional methods using one or more pharmaceutically acceptable excipients or diluents.

The compounds according to the invention may therefore be formulated for oral, buccal, local, parenteral or rectal administration, oral administration being preferred. For oral administration, the medicament may be provided, for example, in the form of tablets, capsules, powders, solutions, syrups or suspensions prepared by the conventional methods, using acceptable diluents. For buccal administration, the medicaments may be presented in the form of tablets or sachets formulated in the usual manner.

The compounds according to the invention may also be made up into preparations for parenteral administration by bolus injection or continuous infusion. Formulations for injection may be prepared as ampoules of unit doses or in multiple dose containers with added preservatives.

The medicaments may assume forms such as suspensions, solutions or emulsion in oily or aqueous carriers, and they may contain formulating auxiliaries such as stabilizers and/or dispersing agents. Alternatively, the active ingredient may be presented in powder form to be reconstituted with a suitable carrier such as sterile, pyrogen-free water before use.

The compounds according to the invention may also be made up into preparations for rectal administration, such as suppositories or retention enemas containing, for example, the usual suppository excipients such as cocoa butter or other glycerides.

For local application, the compounds according to the invention may be incorporated in the usual formulations for ointments, creams, gels, lotions, powders or sprays.

For oral administration, a suitable daily dose of compounds according to the invention consists of 1 to 4 doses amounting to a total of 5 mg to 1 g per day, preferably 5 to 250 mg per day, depending on the patient's condition. In individual cases, it may be necessary to deviate from these quantities, depending on the individual response to the active ingredient or to the nature of its formulation and the time or interval of time at which it is administered. Thus, for example, in certain cases it will be sufficient to use less than the minimum quantity indicated above, whereas in other cases it will be necessary to exceed the maximum quantity indicated.

Compared with known medicaments recognized as highly effective in the same direction, the compounds according to the invention are distinguished by their improved pharmacological activity. This is demonstrated by the results of the pharmacological comparison tests described below.

One recognized method of determining the $H_2$-antagonistic activity is the determination of the $pA_2$-values in vitro on isolated guinea-pigs' atrium (see Ariens, Molecular Pharmacology, Volume 1, Academic Press, New York, 1964).

|  | $pA_2$-values |  |
| --- | --- | --- |
| Cimetidine | 6.21 | Comparison |
| Example 4 | 8.14 |  |

Other compounds corresponding to the general formula I manifest similar pharmacological activities.

EXAMPLE OF PREPARATION (1) Preparation of
2-[2-Hydroxy-3-[3-(piperidylmethyl)benzyloxy]-propyl]-1H-isoindole-1,3-dione A mixture of 10.25 g (0.05 mol) of 3-(1-piperidylmethyl)-benzyl alcohol and 10.15 g (0.05 mol) of N-(2,3-epoxypropyl)-phthalimide is stirred under nitrogen for 80 minutes at 130° C. The viscous resin obtained is chromatographed on silica gel, using methylene chloride/methanol 9:1. The main fraction yields 8.60 g (42%) of the title compound in the form of a light brown oil after concentration by evaporation.

(2) Preparation of
2-Hydroxy-3-[3-(1-piperidylmethyl)-benzyloxy]-propylamine 8.60 g (0.021 mol) of 2-[2-hydroxy-3-[3-(1-piperidylmethyl)-benzyloxy]propyl]-1H-isoindole-1,3-dione and 3.3 ml of hydrazine hydrate (80%) are boiled in 80 ml of ethanol for 3 hours. The residdue left after concentration of the mixture by evaporation is taken up in 50 ml of water; 8 ml of conc. hydrochloric acid are added and the reaction mixture is filtered. The filtrate is adjusted to pH 12 with conc. sodium hydroxide solution and extracted with 3×40 ml methylene chloride. The organic phase is dehydrated with Na₂SO₄ and concentrated by evaporation under vacuum. The residue is distilled in a high vacuum. 4.44 g (76%) of a colourless oil, boiling point 145°–155° C./1×10⁻² mbar are obtained.

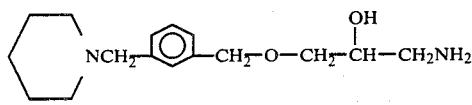

(3) Preparation of 1-Chloro-3-dibenzylamino-2-propanol 49.3 g (0.25 mol) of dibenzylamine and 25.4 g (0.275 mol) epichlorohydrin are stirred under nitrogen at 85°90° C. for 3 hours. The golden yellow oil obtained is distilled in a high vacuum. 50.5 g (70%) of a colourless oil are obtained.

B.p. 150°–155° C. (1.5×10⁻² mbar)

(4) Preparation of 2-Dibenzylaminomethyl-oxirane 50.7 g (0.175 mol) of 1-chloro-3-dibenzylamino-2-propanol, 9.5 g (0.24 mol) of sodium hydroxide and 5 ml of water are stirred together for 1 hour at 95° C. After the addition of 50 ml of chloroform and 20 ml of water, the phases are separated and the organic phase is washed with 20 ml of water, dehydrated with sodium sulphate and concentrated by evaporation. Vacuum distillation of the yellow oil obtained yields 33.7 g (76%) of the oxirane as a colourless oil.

B.p. 125° C. (1.5×10⁻² mbar)

(5) Preparation of 1-Dibenzylamino-3-[3-(3-(1-piperidylmethyl)phenyl]-2-propanol 10.2 g (0.04 mol) of 3-(1-piperidylmethyl)-bromobenzene in 20 ml of tetrahydrofuran are added dropwise to 0.97 g (0.04 mol) of magnesium filings in 5 ml of tetrahydrofuran at a reaction temperature of 60° C. The reaction mixturre is thereafter stirred for 30 minutes at 60° C. and the solution is cooled to 10° C. 10.2 g (0.04 mol) of 2-dibenzylaminomethyl-oxirane in 20 ml of tetrahydrofuran are slowly added dropwise and the resulting solution is stirred at room temperature for 2 hours. After the addition of 20 ml of ice water and 4.5 g of ammonium chloride, the aqueous phase is separated and extracted with 25 ml of methylene chloride. After dehydration with sodium sulphate and concentration by evaporation, the combined organic phases yield a yellow resin which is chromatographed with methylene chloride/methanol (9:1) on silica gel. The second fraction yields the title compound as a pale yellow oil after it has been concentrated by evaporation.

Yield: 11.5 g (67%).

(6) Preparation of 1-Amino-3-[3-(1-piperidylmethyl)phenyl]-2-propanol 11.5 g (0.027 mol) of 1-dibenzylamino-3-[3-(1-piperidylmethyl)phenyl]-2-propanol in 90 ml of ethanol and 10 ml of water are hydrogenated at 35° C. and atmospheric pressure in the presence of 0.5 g of palladium/active charcoal (10% Pd). After removal of the catalyst by filtration and evaporation of the solvent, the residue consists of 5.8 g of a colourless oil which, after chromatographic purification with methanol/conc. ammonia (95:5), yields 3.5 g (52%) of the title compound in the form of a colourless oil.

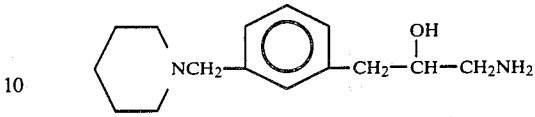

(7) Preparation of 2-Hydroxy-3-[3-(1-piperidylmethyl)phenyl]-butyronitrile 0.74 g (3.2 mmol) of 2-[3-(1-piperidylmethyl)phenyl]-methyl-oxirane, 0.294 g (6 mmol) of sodium cyanide and 0.107 g (2 mmol) of ammonium chloride are boiled in 5 ml ethanol/5 ml water for 6 hours. After substantial concentration of the mother liquor by evaporation under vacuum, the residue is taken up in 10 ml of water, and the solution is adjusted to pH 12 with potassium carbonate and extracted with 3×20 ml of methylene chloride. The organic phase yields 0.82 g of a brown oil after dehydration and evaporation under vacuum.

(8) Preparation of 4-Amino-1-[3-(1-piperidylmethyl)phenyl]-2-butanol 0.10 g (2.6 mmol) of lithium aluminium hydride is added to 0.82 g (3.2 mmol) of 2-hydroxy-3-[3-(1-piperidylmethyl)phenyl]-butyronitrile in 30 ml of ether and 10 ml of tetrahydrofuran and the mixture is heated to reflux for 2 hours. After the addition of 0.25 ml of water, the precipitate formed is suction filtered, suspended in 20 ml of methylene chloride and again suction filtered. After dehydration of the combined organic phases and concentration by evaporation under vacuum, 0.65 g of a yellow oil is obtained as residue which is distilled in a high vacuum to yield 0.51 g (61%) of the title compound.

Colourless, viscous oil, b.p. 140°–150° C./7×10⁻³ mbar.

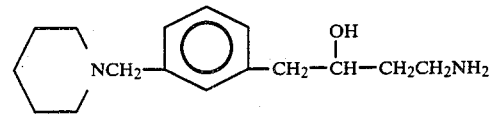

(9) Preparation of 2-[2-Hydroxy-3-[5-(1-piperidylmethyl)-2-thienylthio]-propyl]-1H-isoindole-1,3-dione A mixture of 6.84 g (20 mmol) of 5-(1-piperidylmethyl)-2-S-isothiourea-methylthiophene dihydrochloride and 6.1 g (30 mmol) of N-(2,3-epoxypropyl)-phthalimide is introduced into 50 ml of ethanol, and a solution of 2.4 g (60 mmol) of NaOH in 60 ml of ethanol is slowly added at 0°–5° C. The mixture is left to react for one hour at 0°–5° C. and then for 3 hours at room temperature. The reaction solution is concentrated by evaporation under vacuum, the residue is taken up in CH₂Cl₂/MeOH (80:20), and the organic phase is washed with water until neutral, dehydrated over Na₂SO₄ and concentrated by evaporation under vacuum. 8.3 g (96%) of the title compound are obtained as a brown oil.

(10) Preparation of 2-Hydroxy-3-[5-(piperidylmethyl)-2-thienylthio]-propylamine 8.60 g (20 mmol) of 2-[2-hydroxy-3-[5-(1-piperidylmethyl)-2-thienylthio]propyl]-1H-isoindole-1,3-dione and 3,3 ml of hydrazine hydrate (80%) are boiled in 80 ml of ethanol for 3 hours. The residue obtained after concentration of the mixture by evaporation is taken up in 50 ml of water; 8 ml of conc. hydrochloric acid are added and the reaction mixture is filtered. The filtrate is adjusted to pH 12 with conc. sodium hydroxide solution and extracted with 3×40 ml methylene chloride. The organic phase is dehydrated with Na₂SO₄ and concentrated by evaporation under vacuum. 4.9 g (82% of theoretical) of the title compound are obtained as a light green oil.

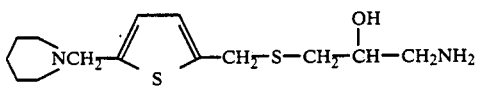

EXAMPLE 1

Preparation of 1-N-[3-(3-piperidylmethyl)-phenoxy-2-hydroxy-propyl]-2-N'-[3-(3-piperidylmethyl)-phenoxypropyl]-diaminocyclobutene-3,4-dione

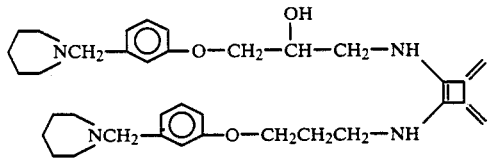

6.78 g (30 mmol) of squaric acid dibutyl ester are reacted with 7.44 g (30 mmol) of (3-piperidylmethyl-phenoxy)-propylamine in 45 ml of absolute ethanol for 6 hours at room temperature. 7.92 g (30 mmol) of (3-piperidylmethyl-phenoxy)-2-hydroxypropylamine are then added and the mixture is left to react for 4 hours. The solid precipitate obtained is suction filtered and recrystallised from ethanol.

Colour crystals, melting point 152°–156° C.
RF=0.48 (C₂H₅OH/N(C₂H₅)₃ 97:3).
Yield: 12.8 g (72% of theoretical).
C₃₄H₄₆N₄O₅ (590.8) Calculated: C 69.12 H 7.85 N 9.48; Found: C 69.21 H 7.74 N 9.77.

¹H-NMR spectrum: (d₆-DMSO, TMS as internal standard) δ=1.20–1.67 (m) 2H. 2.00 (m) 2H, 2.20 –2.43 (m) 8H, 3.37 (s) 4H, 3.53–3.87 (m) 4H, 3.93–4.20 (m) 5H, 5.43 (s, broad) (replaceable by D₂O) 1H, 6.70–7.33 (m) 8H, 7.90 (m) (replaceable by D₂O) 2H ppm.

EXAMPLE 2

Preparation of 1,2-bis-N,N'-[3-(3-Piperidylmethyl)-phenoxypropyl]-diamino-cyclobutene-3,4-dione

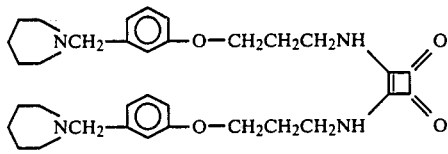

The compound is prepared by a method analogous to that of Example 1 from 6.87 g (30 mmol) of squaric acid dibutylester and 14.88 g (60 mmol) of (3-piperidylmethyl-phenoxy)-propylamine.

Colourless crystals, melting point 158°–160° C.
Rf=0.49 (C₂H₅OH/N(C₂H₅)₃ 97:3).
Yield: 12 g (70% of theoretical).
C₃₄H₄₆N₄O₄ (574.8) Calculated: C 71.04 H 8.07 N 9.75; Found: C 70.81 H 7.81 N 9.79.

¹H-NMR spectrum: (CF₃ COOD, TMS as internal standard) δ=1.40–2.50 (m) 16H, 2.80–3.27 (m) 4H, 3.50–3.83 (m) 4H, 4.00–4.47 (m) 12H, 6.93–7.60 (m) 8H ppm.

EXAMPLE 3

Preparation of 1,2-bis-N,N'-[3-(3-Piperidylmethyl)-phenoxy-2-hydroxypropyl]-diamino-cyclobutene-3,4-dione

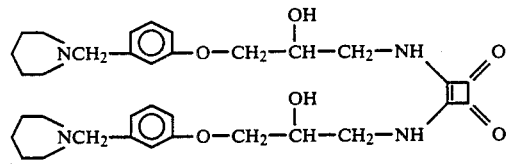

The method of preparation is analogous to that of Example 1, using 6.87 g (30 mmol) of squaric acid dibutyl ester and 15.84 g (60 mmol) of (3-piperidylmethyl-phenoxy)-2-hydroxypropylamine.

Colourless crystals, melting point 108°–110° C.
Rf=0.46 (C₂H₅OH/N(C₂H₅)₃ 97:3).
Yield: 10.36 g (57% of theoretical).
C₃₄H₄₆N₄O₆ (606.8) Calculated: C 67.30 H 7.64 N 9.23; Found: C 67.27 H 7.53 N 9.00.

¹H-NMR spectrum: (d₆-DMSO, TMS as internal standard) δ=1.20–1.67 (m) 12H, 2.17–2.47 (m) 8H, 3.40 (s) 4H, 3.50–4.13 (m) 10H, 5.43 (s, broad) (replaceable by D₂O) 2H, 6.70–7.33 (m) 8H, 7.67 (t) (replaceable by D₂O) 2H ppm.

EXAMPLE 4

Preparation of 3,4-bis[2-Hydroxy-3-(1-piperidylmethyl)phenoxy]-propyl]-amino-1,2,5-thiadiazole-1-oxide

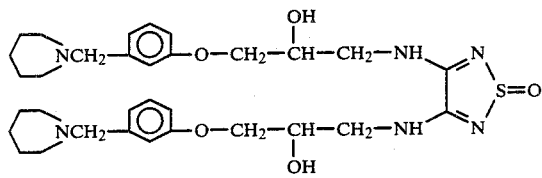

The compound is prepared by a method analogous to that of Example 1 from 9.0 g (30 mmol) of 3,4-diethoxy-1,2,5-thiadiazole-1-oxide and 15.84 g (60 mmol) of (3-piperidylmethyl-phenoxy)-2-hydroxy-propylamine.

Colourless crystals, melting point 129°–130° C.

Rf=0.60 (CH$_3$OH/NH$_3$ conc. 95:5).

Yield: 6.9 g (37% of theoretical).

C$_{32}$H$_{46}$N$_6$O$_5$S (626.8).

$^1$H-NMR spectrum: (CDCl$_3$, TMS as internal standard) δ=1.20–1.73 (m) 12H, 2.17–2.47 (m) 8H, 3.33 (s) 4H, 3.50–3.77 (m) 4 H, 3.78–4.00 (m) 4H, 4.27 (m) 2H, 5.93 (m, broad) (replaceable by D$_2$O)4H, 6.53–7.20 (m) 8H ppm.

EXAMPLE 5

Preparation of 1,2-bis-N,N'-[[3-[5-dimethylaminomethylfuranyl-2-methyl]-thio]ethylamine]-cyclobutene-3,4-dione

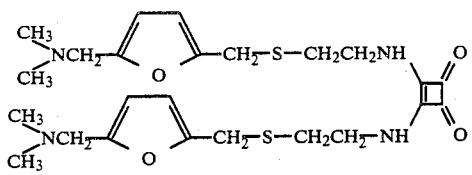

The compounds prepared by a method analogous to that of Example 1 from 6.87 g (30 mmol) of squaric acid dibutylester and 12.84 g (60 mmol) of [5-dimethylaminomethylfuranyl-2-methyl]-thioethylamine.

Colourless crystals, melting point 104°–106° C.

Rf=0.35 (C$_2$H$_5$OH/N(C$_2$H$_5$)$_3$ 97:3).

Yield: 7.13 g (47% of theoretical).

C$_{24}$H$_{34}$N$_4$O$_4$S$_2$ (506).

$^1$H-NMR spectrum (d$_6$-DMSO, TMS as internal standard) δ=2.17 (s) 12H, 2.67 (t) 4H, 3.37 (s) 4H, 3.67 (t) 4H, 3.80 (s) 4H, 6.23 (m) 4H, 7.67 (t, broad) (replaceable by D$_2$O) 2H ppm.

EXAMPLE 6

Preparation of 1-N'-[3-(3-piperidylmethyl)-phenoxy-propyl]-2-N'-[[3-[5-dimethylaminomethylfuranyl-2-methyl]-thio]-ethyl]-diaminocyclobutene-3,4-dione

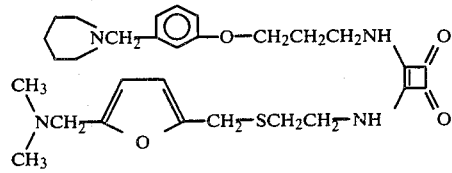

The compound is prepared by a method analogous to that of Example 1 from 6.87 g (30 mmol) of squaric acid dibutylester, 7.44 g (30 mmol) of (3-piperidylmethyl-phenoxy)-propylamine and 6.42 g (30 mmol) of [5-dimethylaminomethylfuranyl-2-methyl]-thioethylamine.

Amorphous solid substance

Rf=0.40 (C$_2$H$_5$OH/N(C$_2$H$_5$)$_3$ 97:3).

Yield: 9.07 g (56% of theoretical).

C$_{29}$H$_{40}$N$_4$O$_4$S (540)

$^1$H-NMR spectrum: (d$_6$-DMSO, TMS as internal standard) δ=1.45 (m) 6H, 2.00 (t) 2H, 2.13 (s) 6H, 2.30 (m) 4H. 2.67 (t) 4H, 3.37 (s) 2H, 3.50–3.87 (m) 6H, 4.00 (t) 2H, 6.17 (m) 2H, 6.67–7.33 (m) 4H, 7.60 (broad) (replaceable by D$_2$O) 2H ppm.

We claim:

1. A compound of the formula

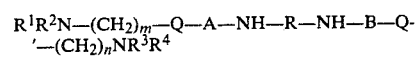

wherein m and n have, independently of one another, the value 0 or 1, R$^1$, R$^2$, R$^3$ and R$^4$, which may be identical or different, each represent hydrogen, C$_{1-10}$-alkyl, C$_{5-6}$-cycloalkyl, amino, lower alkylamino or di-lower alkylamino or R$^1$ and R$^2$ and/or R$^3$ and R$^4$ represent, together with the nitrogen atom attached thereto, a pyrrolidine, methylpyrrolidine, morpholine, thiomorpholine, piperidine, methylpiperidine, N-methylpiperazine, homopiperidine, heptamethyleneimino or octamethyleneimino ring, or R$^3$ and R$^4$ together represent the group (NH$_2$)$_2$C=, or, when m has the value 0, R$^1$ and R$^2$ may together represent the group (NH$_2$)$_2$C=, Q and Q' denote, independently of one another, a furan, thiophene, thiazole or benzene ring, A and B represent, independently of one another, a group O—(CH$_2$)$_q$, O—CH$_2$—CHOH—CH$_2$ or CH$_2$—X—CH$_2$—Y—(CH$_2$)$_p$, q has the value 2, 3 or 4, X represents a sulphur or oxygen atom or the group CHOH, Y represents a single bond or the group CHOH, p has the value 1 or 2 and R represents the ring system

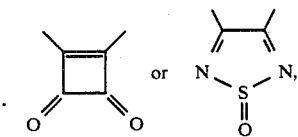

and the physiologically acceptable salts and hydrates thereof.

2. A compound according to claim 1, characterised in that m and n each have the value 1, $R^1$, $R^2$, $R^3$ and $R^4$, which may be identical or different, each represent $C_{1-3}$-alkyl or $C_{5-6}$-cycloalkyl or $R^1$ and $R^2$ and/or $R^3$ and $R^4$ represent, together with the nitrogen atom attached thereto, a pyrrolidine, methylpyrrolidine, morpholine, thiomorpholine, piperidine, methylpiperidine, N-methylpiperazine, homopiperidine, heptamethyleneimino or octamethyleneimino ring, Q represents a benzene ring inserted in the remainder of the molecule in the 1,3- or 1,4-position, A represents the group $O-(CH_2)_q$, $O-CH_2-CHOH-CH_2$ or $CH_2-O-CH_2-CHOH-CH_2$, R represents a group corresponding to the formula

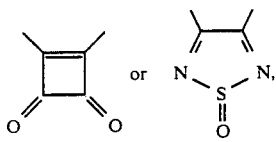

B represents the group $O-(CH_2)_q$, $O-CH_2)_q$, $O-CH_2-CHOH-CH_2$ or $CH_2-O-CH_2-CHOH-CH_2$ and Q' represents a benzene ring inserted in the remainder of the molecule in the 1,3- or 1,4-position.

3. A compound according to claim 1, characterised in that m and n each have the value 1, $R^1$, $R^2$, $R^3$ and $R^4$, which may be identical or different, each represent $C_{1-3}$-alkyl or $C_{5-6}$-cycloalkyl or $R^1$ and $R^2$ and/or $R^3$ and $R^4$ represent, together with the nitrogen atom attached thereto, a pyrrolidine, methylpyrrolidine, morpholine, thiomorpholine, piperidine, methylpiperidine, N-methylpiperazine, homopiperidine, heptamethyleneimino or octamethyleneimino ring, Q represents a benzene ring inserted in the remainder of the molecule in the 1,3- or 1,4-position, A represents the group $O-(CH_2)_q$, $O-CH_2-CHOH-CH_2$ or $CH_2-O-CH_2-CHOH-CH_2$, B represents the group $CH_2-CHOH-CH_2$ or $CH_2-CHOH-CH_2CH_2$, and Q' has the same meaning as Q.

4. A compound according to claim 1, characterised in that m and n each have the value 1, Q represents a benzene ring inserted in the remainder of the molecule in the 1,3- or 1,4-position, A represents the group $O-(CH_2)_q$, $O-CH_2-CHOH-CH_2$, $CH_2-O-CH_2-CHOH-CH_2$, $CH_2-CHOH-CH_2$ or $CH_2-CHOH-CH_2CH_2$, B represents the group $CH_2-S-CH_2CH_2$ or $CH_2-S-CH_2-CHOH-CH_2$, and Q' represents a furan or thiophene ring, the furan ring being inserted in the remainder of the molecule in the 2,5-position and the thiophene ring in the 2,4- or 2,5-position.

5. A compound according to claim 1, characterised in that m and n each have the value 1, Q represents a furan ring inserted in the remainder of the molecule in the 2,5-position or a thiophene ring inserted in the remainder of the molecule in the 2,4- or 2,5-position, A represents the group $CH_2-S-CH_2CH_2$ or $CH_2-S-CH_2-CHOH-CH_2$, B represents the group $CH_2-S-CH_2CH_2$ or $CH_2-S-CH_2-CHOH-CH_2$, and Q' represents a furan or thiophene ring, the furan ring being inserted in the remainder of the molecule in the 2,5-position and the thiophene ring being inserted in the remainder of the molecule in the 2,4- or 2,5-position.

6. A compound according to claim 1, characterised in that m has the value 0, $R^1$ and $R^2$ together represent the group $(NH_2)_2C=$, Q represents a thiazole ring inserted in the remainder of the molecule in the 2,4-position, A represents the group $CH_2-S-CH_2CH_2$, and Q' represents a benzene ring inserted in the remainder of the molecule in the 1,3- or 1,4-position, a furan ring inserted in the remainder of the molecule in the 2,5-position or a thiophene ring inserted in the remainder of the molecule in the 2,5- or 2,4-position.

7. 1-N-[3-piperidylmethyl)-phenoxy-2-hydroxypropyl]-2-N'-[3-(3-piperidylmethyl)-phenoxy-propyl]-diaminocyclobutene-3,4-dione and the physiologically acceptable salts and hydrates thereof.

8. 1,2-bis-N,N'-[3-(3-piperidylmethyl)-phenoxy-2-hydroxypropyl]-diamino-cyclobutene-3,4-dione and the physiologically acceptable salts and hydrates thereof.

9. 3,4-bis-(2-Hydroxy-3-[3-(1-piperidylmethyl)-phenoxy]-propyl]-amino-1,2,5-thiadiazole-1-oxide and the physiologically acceptable salts and hydrates thereof.

10. A compound according to claim 1 selected from the group consisting of 1,2-bis-N,N'-[3-(3-piperidylmethyl)-phenoxy-propyl]-diamino cyclobutene-3,4-dione; 1,2-bis-N,N'-[[3-[5-dimethylaminomethyl-furanyl-2-methyl]-thio]ethylamine]-cyclobutene-3,4-dione; 1-N'-[3-(3-piperidylmethyl)-phenoxypropyl]-2-N'-[[3-[5-dimethylaminomethylfuranyl-2-methyl]-thio]-ethyl-diaminocyclobutene-3,4-dione; and the physiologically acceptable salts and hydrates thereof.

11. A histamine antagonist pharmaceutical preparation, characterised in that it contains a histamine antagonist effective amount of a compound according to one of the claims 1 to 9 and 10 together with an inert, pharmaceutically acceptable excipient or diluent.

* * * * *